United States Patent [19]

Liedek et al.

[11] Patent Number: 4,999,134
[45] Date of Patent: * Mar. 12, 1991

[54] ZINC SALTS, LEAD SALTS AND/OR CALCIUM SALTS OF CARBOXYLIC ACIDS AND THEIR USE AS CORROSION INHIBITORS

[75] Inventors: Egon Liedek, Esslingen; Gerhard Haegele, Stuttgart, both of Fed. Rep. of Germany

[73] Assignee: BASF Aktiengesellschaft, Ludwigshafen, Fed. Rep. of Germany

[*] Notice: The portion of the term of this patent subsequent to May 16, 2006 has been disclaimed.

[21] Appl. No.: 248,085

[22] Filed: Sep. 23, 1988

[30] Foreign Application Priority Data

Sep. 25, 1987 [DE] Fed. Rep. of Germany ....... 3732374

[51] Int. Cl.$^5$ ........................................... C07D 211/00
[52] U.S. Cl. ........................... 252/389.51; 252/389.52; 106/14.42; 106/14.43; 106/14.44; 556/120; 546/245
[58] Field of Search ............. 252/391 APS, 392 APS, 252/389.52 APS, 389.51 APS; 106/14.42, 14.43, 14.44; 546/245; 556/120

[56] References Cited

U.S. PATENT DOCUMENTS

| 2,578,725 | 12/1951 | Micheal et al. | 252/391 X |
| 2,908,648 | 10/1959 | Spivack et al. | 252/391 X |
| 3,996,253 | 12/1976 | Magagnoli et al. | 564/86 |
| 4,123,455 | 10/1978 | Conrow et al. | 562/54 |
| 4,329,381 | 5/1982 | Eschewey et al. | 252/391 X |
| 4,830,775 | 5/1989 | Liedek et al. | 252/389.52 |

FOREIGN PATENT DOCUMENTS

| 461662 | 10/1968 | Fed. Rep. of Germany . |
| 2502781 | 5/1978 | Fed. Rep. of Germany . |
| 2807698 | 5/1982 | Fed. Rep. of Germany . |
| 2824508 | 5/1982 | Fed. Rep. of Germany . |
| 3616721 | 1/1983 | Fed. Rep. of Germany . |
| 1353357 | 5/1974 | United Kingdom . |
| 1415996 | 12/1975 | United Kingdom . |
| 1458029 | 12/1976 | United Kingdom . |

OTHER PUBLICATIONS

Chemical Abstracts, vol. 67, 1967, p. 6188, abstract No. 65439c, Magagnoli et al., "Materials for Color Photography".
DE-A-3,616,721 = U.S. Ser. No. 07/048,744.
DE-A-2,947,418 = U.S. Pat. No. 4,344,862.
EP-A-0,068,407 = GB-A-2,100,720.

Primary Examiner—Robert L. Stoll
Assistant Examiner—Valerie Fee
Attorney, Agent, or Firm—Oblon, Spivak, McClelland, Maier & Neustadt

[57] ABSTRACT

Novel zinc salts, lead salts and/or calcium salts of carboxylic acids of the general formula

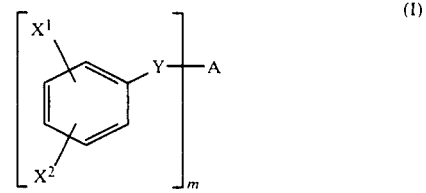

where A is a radical of the formula

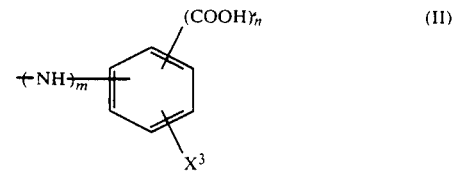

or

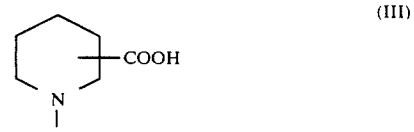

Y is —CO— or —SO$_2$—, X$^1$ is C$_1$–C$_8$-alkyl, C$_1$–C$_8$-alkoxy or halogen, X$^2$ is hydrogen, C$_1$–C$_8$-alkyl or halogen, X$^3$ is hydrogen, nitro or halogen, m and n are each 1 or 2, and X$^1$ may furthermore be hydrogen if A is a radical of the formula (III) or X$^3$ is nitro or m is 2, in particular the basic salts of (I), are suitable as corrosion inhibitors for coating systems.

20 Claims, No Drawings

ZINC SALTS, LEAD SALTS AND/OR CALCIUM SALTS OF CARBOXYLIC ACIDS AND THEIR USE AS CORROSION INHIBITORS

BACKGROUND OF THE INVENTION

A large number of products intended to replace red lead and pigments based on zinc chromate as corrosion inhibitors have already been proposed These substitute products contain, as a rule, metal-containing organic compounds.

Thus, for example, DE-C-25 02 781 describes zinc salts and lead salts and mixtures of these salts based on 5-nitroisophthalic acid as rust-inhibiting additives for coating materials. Among the salts described in this patent, the zinc salt of 5-nitroisophthalic acid in particular is used industrially. However, a disadvantage of the products described in DE-C-25 02 781 is that their action and range of uses are limited. Thus, for example, one complaint is that the action in aqueous coating systems is insufficient.

The zinc salts and lead salts described in DE-A-28 07 698 and 28 24 508 exhibit similar behavior.

SUMMARY OF THE INVENTION

To deal with the constantly changing and complex problems of rust inhibition with the aid of coating materials, it is desirable to provide further active substances having improved properties in various directions. The provision of further active substances which may be regarded as equivalent alternatives to the prior art may in itself constitute a technical advance, since frequently extensive experience is required before advantages in specific industrial applications can be recognized.

It is an object of the present invention to provide further pigments which are suitable for corrosion inhibition and do not have the disadvantages of the known corrosion-inhibiting pigments.

DESCRIPTION OF THE PREFERRED EMBODIMENTS

The present invention relates to zinc salts, lead salts, calcium salts or mixed salts of these metals with carboxylic acids of the general formula

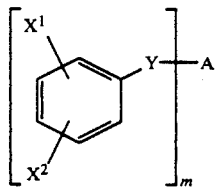

(I)

where A is a radical of the formula

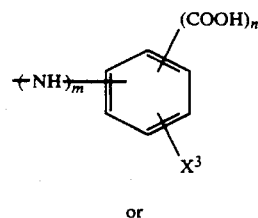

(II)

or

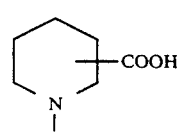

(III)

Y is —CO— or —SO$_2$—, $X^1$ is —C$_1$-C$_8$-alkyl, C$_1$—C$_8$—alkoxy or halogen, $X^2$ is hydrogen, C$_1$—C$_8$—alkyl or halogen, $X^3$ is hydrogen, nitro or halogen, m and n are each 1 or 2, and $X^1$ may furthermore be hydrogen if A is a radical of the formula (III) or $X^3$ is nitro or m is 2.

Compared with the most similar zinc salts and lead salts disclosed in DE-C-25 02 781, the salts of the invention have better corrosion inhibiting properties in nonaqueous coating systems, for example in coating materials consisting of air-drying linseed oil/wood oil alkyd resins. Moreover, the zinc salts and lead salts according to the present invention are also suitable for aqueous coating systems, for example for water-dilutable alkyd resins.

Specific examples of suitable C$_1$-C$_8$-alkyl radicals $X^1$ and $X^2$ are: methyl, ethyl, n-propyl, isopropyl, n-butyl, isobutyl, tert-butyl, n-amyl, isoamyl, 1,1-di- methylprop-1-yl (tert-amyl), n-hexyl, isohexyl, heptyl, n-octyl, isooctyl and 2-ethylhexyl.

Alkyl radicals $X^1$ are preferably C$_1$-C$_4$-alkyl, in particular methyl and ethyl.

For example, methoxy, ethoxy, propoxy, butoxy, pentyloxy and octyloxy may be mentioned as examples of C$_1$-C$_8$-alkoxy, the C$_1$-C$_4$-alkoxy radicals being preferred.

Fluorine, bromine and chlorine may be mentioned as halogen radicals $X^1$, $X^2$ and/or $X^3$, chlorine being preferred.

Because of their properties, zinc salts, lead salts and/or calcium salts of carboxylic acids (I) in which Y is —SO$_2$— are preferred.

Among these, the carboxylic acids (I) in which $X^1$ is C$_1$-C$_4$-alkyl, C$_1$-C$_4$-alkoxy or chlorine, $X^2$ and $X^3$ are each hydrogen and n and m are each 1 are noteworthy.

Particularly preferred compounds (I) are those in which $X^2$ and $X^3$ are each hydrogen, n and m are each 1 and $X^1$ is methyl or ethyl.

Zinc salts, lead salts and/or calcium salts of carboxylic acids of the formula

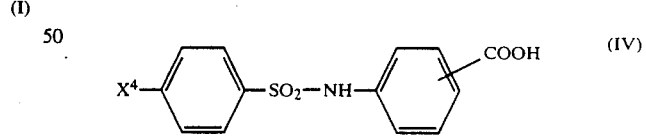

(IV)

where $X^4$ is ethyl or, preferably, methyl and the carboxyl group is in the 2-, 3 -or 4-position, are very particularly preferred.

Lead salts, zinc salts and/or calcium salts of the carboxylic acid

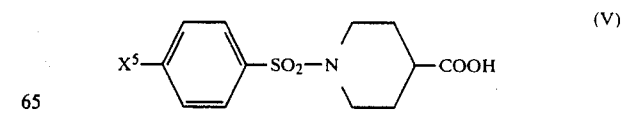

(V)

where $X^5$ is hydrogen or C$_1$-C$_4$-alkyl, preferably methyl or ethyl, in particular hydrogen, may also be mentioned.

Basic zinc salts and/or lead salts of the carboxylic acids (I), (III) and (IV), in which the molar ratio of carboxylic acid to zinc and/or lead is about 1:1, are very particularly preferred.

In the case of the carboxylic acids (IV) and (V), these basic salts are of the formulae

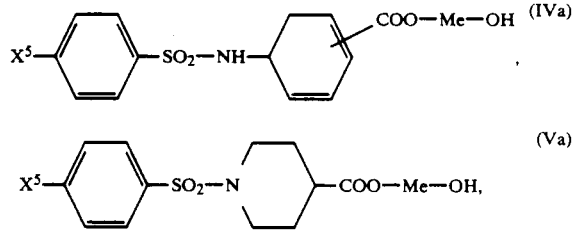

where Me is Zn and/or Pb.

The calcium salts of (I) or (IV) and (V) preferably contain 2 moles of (I), (IV) or (V) per mole of calcium.

The novel salts are present in the liquid coating materials in general in amounts of from 0.2 to 5, preferably from 0.5 to 3, % by weight, based on the solid.

The novel zinc salts, lead salts, calcium salts or mixed salts containing these metals are obtained in a conventional manner, either by reacting the alkali metal salts of the acid (I) with soluble calcium salts, zinc salts, lead salts or their mixtures, such as zinc sulfate, calcium nitrate and/or lead nitrate, or by reacting the free acid (I) with zinc oxide, lead oxide and/or calcium oxide in an aqueous medium at elevated temperatures.

By varying the molar ratio of carboxylic acid (I) to zinc compounds, lead compounds, calcium compounds or mixtures of these, the concentration, the temperature, the time and the pH, pure, ie. defined, zinc compounds, lead compounds or zinc/lead compounds of different basicity are obtained.

If (I) is reacted with calcium compounds, the neutral salts are obtained.

The neutral salts of (I) are obtained, as a rule, using a ratio of two equivalents of carboxylic acid to 2 equivalents (=1 mole) of zinc compound, lead compound and/or calcium compound in a neutral reaction medium. To prepare the basic salts, 2 equivalents (=1 mole) of zinc oxide and/or lead oxide are used per equivalent of carboxylic acid, the resulting higher pH being sufficient for the formation of the basic salts. If, instead of the oxides, the corresponding water-soluble salts are used, the equivalent amount of bases, ie. 2 equivalents per equivalent of carboxylic acid, must be added to the mixture to permit the formation of the basic salts in the alkaline range. If soluble salts of the metals are used, the alkaline solution of the acid is advantageously initially taken.

Suitable bases are, in particular, the alkali metal hydroxides, such as sodium hydroxide and potassium hydroxide, in the form of the aqueous solutions.

The aqueous reaction mixture is kept at the desired temperature until the pH of the aqueous phase remains constant. The precipitated salts of (I) are isolated in a conventional manner, washed and dried.

The compound formed is determined in general by comparison of the analytical data, IR spectra and the X-ray diffraction patterns. As a rule, it is not possible to predict whether it will be possible to prepare stable basic zinc salts and/or lead salts from an organic acid.

The Examples which follow illustrate the preparation of the salts.

I. Illustrative Examples

EXAMPLE 1

14.57 g (0.05M) of N-toluenesulfonylanthranilic acid were dissolved in 175 ml of water with the addition of 25 ml of 4N NaOH and with gentle heating. Thereafter, a solution of 14.38 g (0.05M) of $ZnSO_4.7H_2O$ in 50 ml of water was slowly added, the resulting suspension was diluted to 400 ml and stirring was continued for 4 hours at 30° C. until the pH remained constant at pH 8.5. The product was filtered off under suction, washed, and dried at 80° C. Yield: 17.8 g of a product containing 1.14 mole of Zn per mole of starting acid. In the X-ray diffraction pattern, free ZnO was not visible.

EXAMPLE 2

14.57 g (0.05M) of N-toluenesulfonylamino-3-benzoic acid were dissolved in 250 ml of water with the addition of 25 ml of 4 N NaOH at 25° C. Thereafter, 14.38 g (0.05M) of $ZnSO_4.7H_2O$, dissolved in 50 ml of water, were added slowly while stirring, the resulting suspension was diluted to 450 ml and stirring was continued for about 3 hours at 75° C. After stirring of the cold mixture (pH =7.5), filtration under suction, washing and drying at 80° C., 15.2 g of a substance which contained about 1.3 moles of Zn per mole of starting acid were obtained.

EXAMPLE 3

14.57 g (0.05M) of N-toluenesulfonylamino-4-benzoic acid were dissolved in 250 ml of water with the addition of 25 ml of 4N NaOH at 25° C. Thereafter, 14.38 g (0.05M) of $ZnSO_4.7H_2O$, dissolved in 50 ml of water, were slowly added, while stirring. After dilution to a total volume of 450 ml, the mixture was slowly heated to 80° C. and kept at this temperature for 4 hours while stirring, the resulting pH being 6.3. After stirring the cold mixture (23° C., pH =7.3) and working up as in Example 3, 14.9 g of a product which contained 1.36 moles of Zn per mole of starting acid resulted.

EXAMPLE 4

Basic Zn N-benzenesulfonylpiperidine-4-carboxylate 12.12 g (0.045M) of N-benzenesulfonylpiperidine-4-carboxylic acid were dissolved in 250 ml of water with the addition of 22.5 ml of 4N NaOH at 50° C. Thereafter, 2.94 g (0.045M) of $ZnSO_4.7H_2O$, dissolved in 100 ml of water, was slowly added at 50° C. After the mixture had been stirred for 3 1/2 hours at 50° C., the resulting pH was 7.3. The mixture was then stirred at room temperature, and the product was filtered off under suction, washed and dried. 15.8 g of a product which contained 1.05 moles of Zn per mole of starting acid resulted.

EXAMPLE 5

Basic Zn 3,5-di-(benzenesulfonylamino)-benzoate 10.81 g (0.025M) of 3,5-di-(benzenesulfonylamino)-benzoic acid were dissolved in 300 ml of water with the addition of 12.5 ml of 4N NaOH. Thereafter, 7.19 g (0.025M) of $ZnSO_4.7H_2O$, dissolved in 50 ml of water, were slowly added. The resulting suspension was stirred for 3 hours at 23° C. and for a further 3 hours at 75° C. The precipitate was filtered off under suction, washed, and dried at 80° C. Yield: 11.4 g.

EXAMPLE 6

10.06 g (0.03M) of 5-toluenesulfonylaminoisophthalic acid were dissolved in 150 ml of water with the addition of 30 ml of 4N NaOH. After the mixture had been heated to 80° C., 17.25 g (0.06M) of $ZnSO_4.7H_2O$ in 80 ml of water were slowly added. The resulting suspension was kept at 80° C. for 3 hours, while stirring. After stirring of the cold mixture, filtration under suction, washing and drying, 12.4 g of a colorless, ZnO-free substance resulted, which gave a corrosion protection value of 72 in the test according to II.

EXAMPLE 7

Ca N-(p-toluenesulfonyl)-anthranilate 14.56 g (0.05M) of N-p-toluenesulfonylanthranilic acid were dissolved in 50 ml of water with the addition of 50 ml of N NaOH. Thereafter, 5.9 g (0.025M) of $Ca(NO_3)_2.4H_2O$ in 50 ml of water were slowly added, while stirring. After filtration under suction, washing and drying of the precipitate formed, 13.3 g of the desired Ca salt resulted.

II. Testing of performance characteristics

The corrosion protection value of the corrosion-inhibiting pigments was determined in the manner described below:

First, a primer having a pigment volume concentration (PVC) of about 36% is prepared by dispersion for 2 hours with 2 mm glass beads in a vibratory dispersing apparatus, in accordance with the following formulation:

1.5 parts by weight of test substance,
16.5 parts by weight of microtalc,
12.0 parts by weight of micronized calcium carbonate,
10.0 parts by weight of iron oxide red pigment and
75.0 parts by weight of binder solution which contains
32% by weight of a resin-modified linseed oil/wood oil alkyd resin having an acid number of <25 (Alftal AM ® 380 from Farbw.Hoechst AG).

With the aid of a spin coater, unphosphatized, degreased deep-drawn steel sheets (USt 1405) are coated in a manner such that, after drying in the air for 7 days and subsequent drying for 2 hours at 50° C., mean film thicknesses of 40 μm result. The test coatings are scratched in a defined manner and are compared after being subjected to the salt spray test (DIN 50021) for 400 hours.

Evaluation is effected according to a combined system which includes the state of corrosion of the alkali-treated coat substrate, the underrusting at the crack and delamination (determined by means of a peeling test using self-adhesive tape).

The result is a corrosion protection value (CV) which is between zero (=the coating material without test substance) and the theoretically unchanged coating with CV 100. In practice, corrosion protection values of about 50 may be regarded as good, and values above 70 as very good.

Coating materials were prepared with the salts of Examples 1 to 5 in the manner described above. The coated sheets were tested according to DIN 50021 and evaluated after 400 hours.

The amounts of salt used and the CV value are summarized in the Table below.

TABLE

Summary of the results of the corrosion inhibition test

| Salt of Example | Amount [parts by weight] | Corrosion protection value after 400 h | |
|---|---|---|---|
| | | According to the invention | Prior art[1] |
| 1 | 1.5 | 65 | 51 |
| 2 | 1.5 | 73 | 47 |
| 3 | 1.5 | 76 | 47 |
| 4 | 1.5 | 77 | 71 |
| 5 | 1.5 | 74 | 63 |

[1]Zinc 5-nitroisophthalate according to DE-C-25 02 781

The Ca salt prepared according to Example 7 was tested as stated above under II, except that instead of 1.5 parts by weight a mixture of 0.85 parts by weight of basic zonc 5-nitroisophthalate of DE-C-25 02 781 and 0.15 part by weight of the Ca salt of Example 7 were used.

For comparision, an inhibitor which contained only the prior art substance zinc 5-nitroisophthalate was also tested under same conditions.

| Coating contains | Corrosion protection value after 400 h |
|---|---|
| (a) 1.5 parts by weight of basic zinc 5-nitroisophthalate | 54 |
| (b) 1.0 part by weight of basic zinc 5-nitroisophthalate | 44 |
| (c) 0.85 part by weight of basic zinc 5-nitroisophthalate + 0.15 part by weight of Ca salt of Example 7 | 57 |

The results show that, when the Ca compound of Example 7 is also used, the amount of corrosion inhibitor can be reduced without any loss of activity.

We claim:

1. A zinc salt, lead salt or calcium salt, or a mixed salt containing two or three of these metals, of a carboxylic acid of the formula

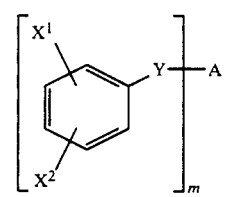

(I)

where A is a radical of the formula

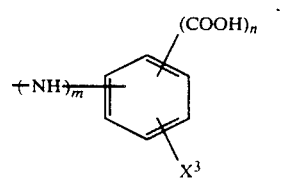

(II)

or

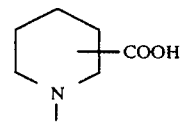

(III)

Y is —CO— or —SO$_2$—, X$^1$ is C$_1$-C$_8$—alkyl, C$_1$-C$_8$—alkoxy or halogen, X$^2$ is hydrogen, C$_1$-C$_8$-alkyl or halogen, X$^3$ is hydrogen, nitro or halogen, m and n are each 1 or 2, and X$^1$ may furthermore be hydrogen if A is a radical of the formula (III) or X$^3$ is nitro or m is 2.

2. A zinc salt, lead salt or calcium salt or a mixed salt thereof as claimed in claim 1, wherein Y is —SO$_2$—.

3. A zinc salt, lead salt or calcium salt or a mixed salt thereof as claimed in claim 1, wherein X$^1$ is C$_1$-C$_4$-alkyl, C$_1$-C$_4$-alkoxy or chlorine, X$^2$ is hydrogen and n and m are each 1.

4. A zinc salt, lead salt or calcium salt or a mixed salt thereof as claimed in claim 2, wherein X$^1$ is C$_1$-C$_4$-alkyl, C$_1$-C$_4$-alkoxy or chlorine, X$^2$ is hydrogen and n and m are each 1.

5. A zinc salt, lead salt or calcium salt or a mixed salt thereof as claimed in claim 3, wherein X$^1$ is methyl or ethyl.

6. A zinc salt, lead salt or calcium salt or a mixed salt thereof as claimed in claim 4, wherein X$^1$ is methyl or ethyl.

7. A zinc salt, lead salt or zinc/lead salt as claimed in claim 1, wherein the molar ratio of carboxylic acid to zinc, lead or a mixture of these is about 1:1.

8. A zinc salt, lead salt or zinc/lead salt as claimed in claim 2, wherein the molar ratio of carboxylic acid to zinc, lead or a mixture of these is about 1:1.

9. A zinc salt, lead salt or zinc/lead salt as claimed in claim 3, wherein the molar ratio of carboxylic acid to zinc, lead or a mixture of these is about 1:1.

10. A zinc salt, lead salt or zinc/lead salt as claimed in claim 4, wherein the molar ratio of carboxylic acid to zinc, lead or a mixture of these is about 1:1.

11. A zinc salt, lead salt or zinc/lead salt as claimed in claim 5, wherein the molar ratio of carboxylic acid to zinc, lead or a mixture of these is about 1:1.

12. A zinc salt, lead salt or zinc/lead salt as claimed in claim 6, wherein the molar ratio of carboxylic acid to zinc, lead or a mixture of these is about 1:1.

13. A calcium salt as claimed in claim 5, wherein the molar ratio of carboxylic acid to calcium is about 2:1.

14. A calcium salt as claimed in claim 6, wherein the molar ratio of carboxylic acid to calcium is about 2:1.

15. A calcium salt as claimed in claim 1, wherein the molar ratio of carboxylic acid to calcium is about 2:1.

16. A zinc salt, lead salt or zinc/lead salt of a carboxylic acid (I) of the formula

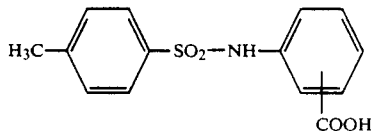

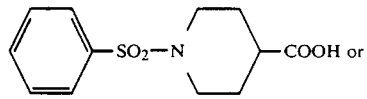

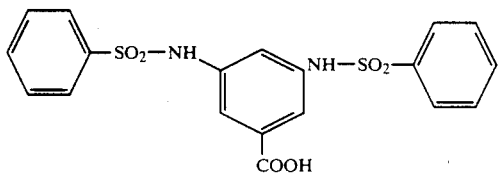

or of a mixture of these carboxylic acids.

17. A zinc salt, lead salt or zinc/lead salt as claimed in claim 16, wherein the molar ratio of carboxylic acid to zinc, lead or zinc and lead is about 1:1.

18. A calcium salt of a carboxylic acid of the formula

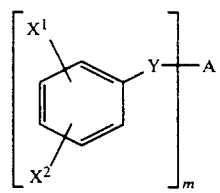

or of a mixture of these carboxylic acids.

19. A calcium salt as claimed in claim 18, wherein the molar ratio of carboxylic acid to calcium is about 2:1.

20. A compound according to claim 1 where A is a radical of the formula (II).

* * * * *